(12) United States Patent
Castaneda et al.

(10) Patent No.: US 10,130,406 B2
(45) Date of Patent: Nov. 20, 2018

(54) HEADLESS BONE COMPRESSION SCREW

(71) Applicant: Biomet Manufacturing, LLC, Warsaw, IN (US)

(72) Inventors: Alfredo Castaneda, Miami, FL (US); Michael Gellatly, Miami Springs, FL (US); Sean Graham, Naples, FL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/404,917

(22) Filed: Jan. 12, 2017

(65) Prior Publication Data

US 2017/0196608 A1 Jul. 13, 2017

Related U.S. Application Data

(63) Continuation-in-part of application No. 14/993,203, filed on Jan. 12, 2016.

(51) Int. Cl.
*A61B 17/86* (2006.01)
*A61B 17/88* (2006.01)
(Continued)

(52) U.S. Cl.
CPC .......... *A61B 17/863* (2013.01); *A61B 17/84* (2013.01); *A61B 17/8645* (2013.01); *A61B 17/8888* (2013.01); *A61B 2017/681* (2013.01)

(58) Field of Classification Search
CPC ... A61B 17/84; A61B 17/8888; A61B 17/863; A61B 17/8645
See application file for complete search history.

(56) References Cited

U.S. PATENT DOCUMENTS 5,403,136 A * 4/1995 Mathys ............... A61B 17/744
411/263
5,562,672 A 10/1996 Huebner et al.
(Continued)

FOREIGN PATENT DOCUMENTS

FR 2760628 A1 9/1998
WO WO-2007109132 A2 9/2007
(Continued)

OTHER PUBLICATIONS

"International Application Serial No. PCT/US2017/013184, International Search Report dated Mar. 24, 2017", 6 pgs.
(Continued)

*Primary Examiner* — Christian Sevilla
(74) *Attorney, Agent, or Firm* — Schwegman Lundberg & Woessner, P.A.

(57) ABSTRACT

Implementations described herein include headless compression screws and corresponding systems. The headless compression screw has a shaft extending along a longitudinal axis from an insertion end to a driving end. The shaft includes a first portion and a second portion. The first portion extends from proximate the insertion end to a first intermediate point and includes a first thread extending along at least a portion thereof that has a constant pitch. The second portion extends from proximate the driving end to a second intermediate point and includes a thread extending along at least a portion thereof that has a variable pitch that decreases from a first value proximate the second intermediate point to a second value proximate the driving end. Methods of reducing a fracture using headless compression screws are also described.

13 Claims, 9 Drawing Sheets

(51) Int. Cl.
    *A61B 17/84*     (2006.01)
    *A61B 17/68*     (2006.01)

(56) References Cited

U.S. PATENT DOCUMENTS

| | | |
|---|---|---|
| 5,871,486 A | 2/1999 | Huebner |
| 5,964,768 A | 10/1999 | Huebner |
| 6,030,162 A | 2/2000 | Huebner |
| 6,984,235 B2 | 1/2006 | Huebner |
| 8,070,786 B2 | 12/2011 | Huebner et al. |
| 8,128,671 B2 | 3/2012 | Taylor |
| 9,161,793 B2 | 10/2015 | Huebner |
| 2013/0211468 A1 | 8/2013 | Huebner |
| 2014/0277190 A1 | 9/2014 | Splieth et al. |
| 2015/0201984 A1* | 7/2015 | Orbay .................. A61B 17/863 606/304 |
| 2017/0196612 A1 | 7/2017 | Castaneda et al. |

FOREIGN PATENT DOCUMENTS

| | | |
|---|---|---|
| WO | WO-2015100149 A1 | 7/2015 |
| WO | WO-2017123753 A1 | 7/2017 |

OTHER PUBLICATIONS

"International Application Serial No. PCT/US2017/013184, Written Opinion dated Mar. 24, 2017", 8 pgs.

"U.S. Appl. No. 14/993,203, Non Final Office Action dated Dec. 5, 2017", 8 pgs.

"U.S. Appl. No. 14/993,203, Response filed May 7, 2018 to Non Final Office Action dated Dec. 5, 2017", 13 pgs.

* cited by examiner

HEADLESS BONE COMPRESSION SCREW

PRIORITY APPLICATIONS

This application is a continuation-in-part application of U.S. patent application Ser. No. 14/993,203, filed Jan. 12, 2016, the content of which is hereby incorporated by reference in its entirety.

BACKGROUND

One method of reducing a fracture across two bone fragments is driving a compression screw across the fracture site. Some compression screws can have a variable thread pitch along the length of the screw to aid in compressing the fracture. For fractures distal from the surface of the bone, it can be desirable to have a compression screw with no head, such that the screw can be inserted deeply into the bone. One example of such a fracture is a proximal third fracture of the scaphoid. Generally, after the fracture has healed, the compression screw or screws can be removed.

SUMMARY

The present inventors have recognized, among other things, that a problem to be solved can include the lack of appropriate tactile feedback to surgeons that are implanting certain compression screws. Surgeons can have difficulty ascertaining whether the certain screws have been advanced far enough to fully reduce the fracture because the torsional resistance experienced by the surgeon turning the compression screw does not correlate to the compression of the bone fragments. Some designs are also not effective enough at providing sufficient compression between the two bone fragments and can be difficult to remove after the fracture has healed. The present subject matter can help provide a solution to this problem, such as by providing a headless compression screw comprising a shaft extending along a longitudinal axis from an insertion end to a driving end. A driving end of the shaft can comprise a driving engagement feature. The shaft can further comprise a first portion and a second portion. The first portion can extend from proximate the insertion end to a first intermediate point along the longitudinal axis. The first portion can comprise a first thread extending across at least a portion of the first portion and having a constant pitch. The second portion can extend from proximate the driving end to a second intermediate point that is proximal to the first intermediate point. The second portion can comprise a second thread extending across at least a portion of the second portion and can have a variable pitch that decreases from a first value proximate the second intermediate point to a second value proximate the driving end. The work required to advance the shaft through a first bone tissue segment is less than the work required to advance the shaft through both the first bone tissue segment and a second bone tissue segment. The ratio of the work required to advance the first end of the shaft through the first bone tissue segment and the second bone tissue segment prior to engagement of the second portion and upon engagement of the second portion in the first bone tissue segment can be at least about 1:1.5.

The present description also provides for a method of reducing a fracture between a proximal and distal bone fragment the method. The method can include driving an insertion end of a headless compression screw through the proximal bone fragment and into the distal bone fragment. The shaft can comprise a first portion that can include a first thread that can have a constant pitch. A driving end of the headless compression screw can be driven through the distal bone fragment. The shaft can comprise a second portion that includes a second thread having a varying pitch. The pitch can vary continuously as distance from the driving end decreases. Driving the second portion through the proximal bone fragment can compress the distal bone fragment and proximal bone fragment together. In one example, torque required to drive the second end through the proximal bone fragment can be correlated to the compressive force between the proximal and distal bone fragments, such that before compression occurs, both the torque and compression are both near zero, and as compression begins to occur, both torque and compression increase proportionally.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
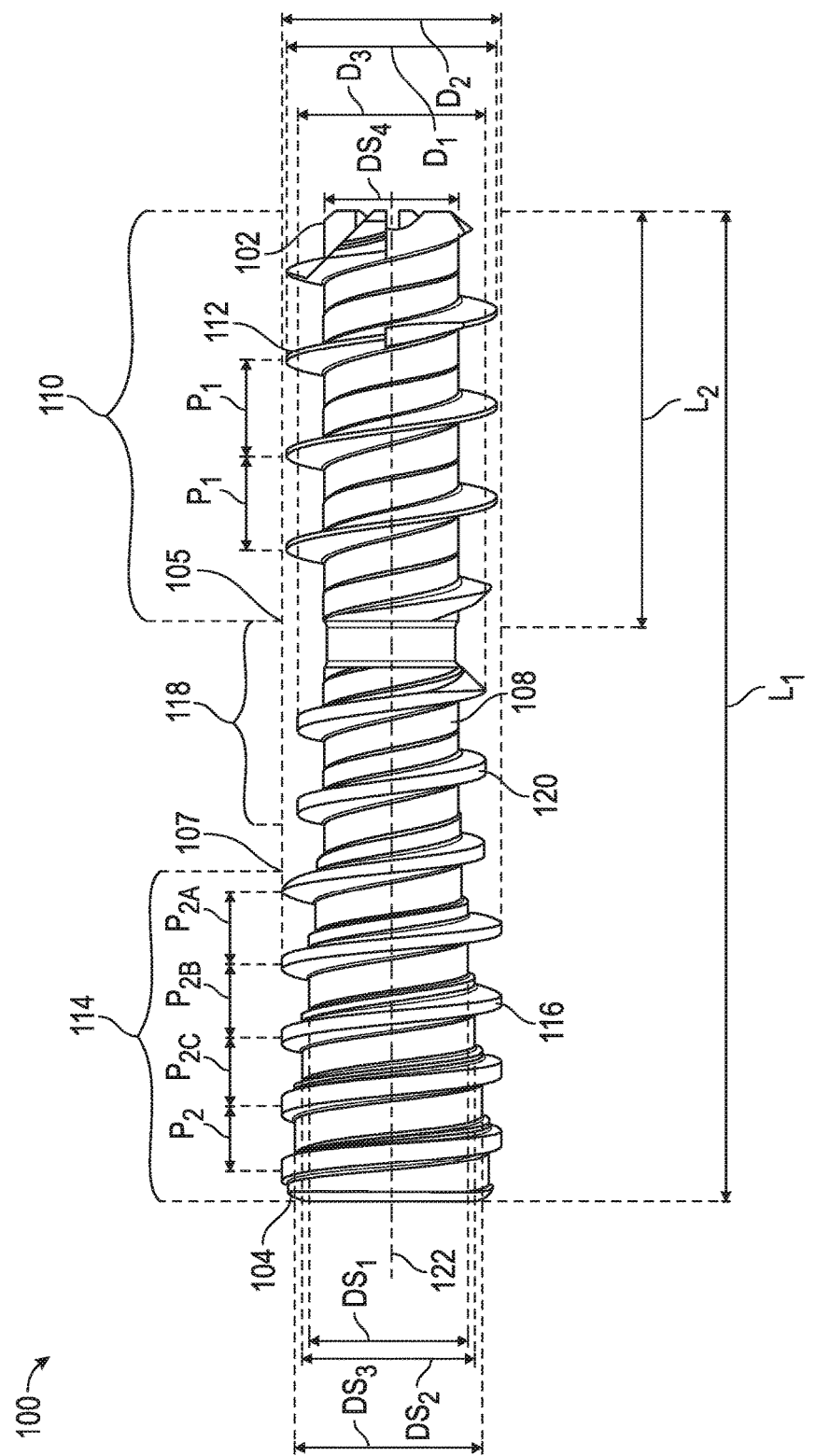
FIG. 1 is a side view of a compression screw according to an example of the present description.
Figure 2:
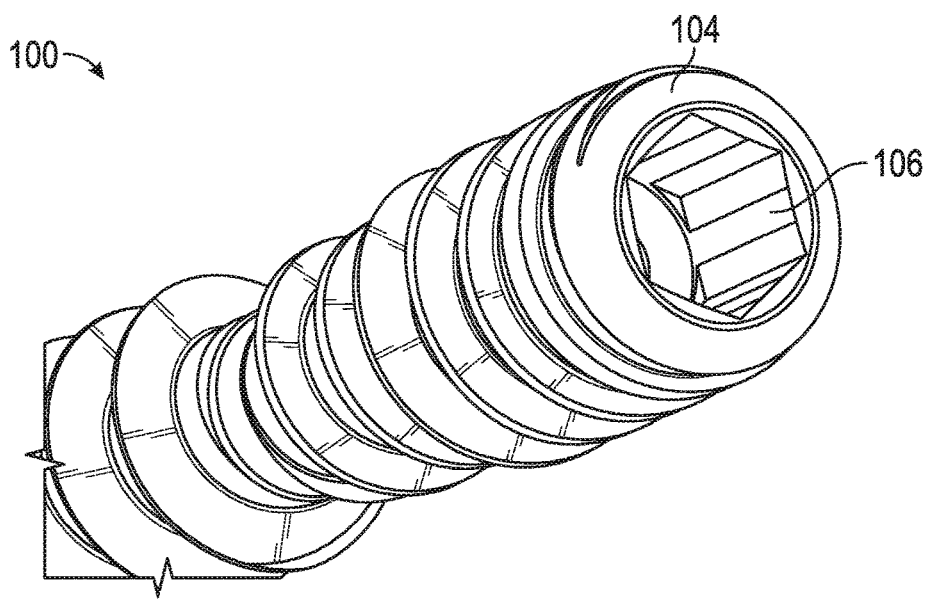
FIG. 2 is a perspective second end view of a compression screw according to an example of the present description.
Figure 3:
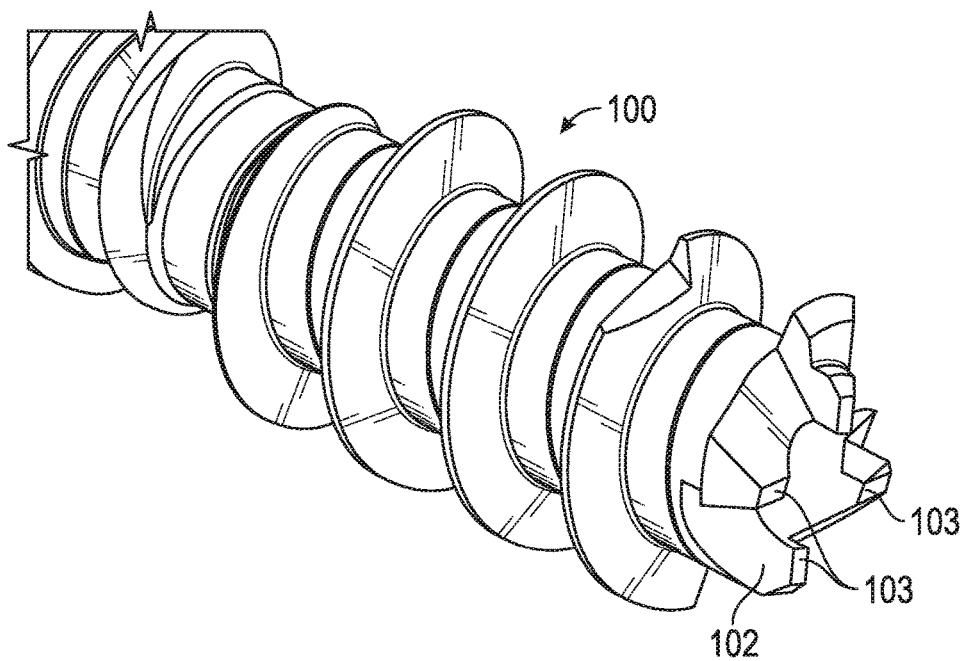
FIG. 3 is a perspective first end view of a compression screw according to an example of the present description.

FIG. 1 illustrates a headless compression screw 100 according to an example in the present description. Headless compression screw 100 can include an insertion end 102 that is configured for insertion into a bone. Headless compression screw 100 can further include a driving end 104 opposite the insertion end 102. The driving end 104 can include a driver engagement feature 106 disposed therein (e.g., illustrated in FIG. 2). As shown, the driver engagement feature 106 can include a female hexagonal feature formed into the driving end 104. However, other shaped features are also contemplated (both male and female). For example, the driver engagement feature 106 can include a cruciate shape, square shape, six-point star shape, or the like. Where a hexagonal (or "hex") feature is used, the headless compression screw 100 can be driven by a driver that can include a male hexagonal engagement portion. The driver can engage the headless compression screw, such as via the female hex feature, and facilitate driving the headless compression screw across a bone fracture. A perspective view of the insertion end 102 of headless compression screw 100 is provided in FIG. 3. This view illustrates an example of the flutes 103 present at insertion end 102 that can aid in the headless compression screw's self-drilling and self-tapping capability. The sharpened nature of the flutes 103 can help assure that a distal bone segment is not distracted when the drill is being inserted through the proximal and then distal bone segments.

Returning to FIG. 1, a shaft 108 extends from the insertion end 102 to the driving end 104. The headless compression screw 100 can include a first portion 110 extending from proximate the insertion end 102 to a first intermediate point 105. First portion 110 can include a first thread 112 that can extend across at least a portion of the first portion 110 and can have a constant pitch, $P_1$. The headless compression screw can further include a second portion 114 that can extend from proximate the driving end 104 to a second intermediate point 107. The second portion 114 can include a second thread 116 that can extend across at least a portion of the second portion 114 and can have a variable pitch (e.g., $P_{2A}$, $P_{2B}$, $P_{2C}$, etc.). The variable pitch of the second thread 116 can decrease from a first value proximate the second intermediate point to a second value proximate the driving end as a distance from the driving end 104 decreases (i.e., $P_{2C} < P_{2B} < P_{2A}$, and the like). The largest pitch (e.g., $P_{2A}$) of the second portion 114 can be less than or equal to the constant pitch $P_1$ of the first portion 110. In an example, the pitch $P_2$ of the second threads 116 in second portion 114 can be close to 1.0 mm immediately proximate second end 104 (or between about 0.9 mm and about 1.1 mm), and the pitch $P_2$ of the threads closest to first portion 110 can be close to 1.3 mm (or between about 1.2 mm and about 1.4 mm). The fixed pitch $P_1$ of a first thread 112 in first portion can be about 1.5 mm (or between 1.4 mm and about 1.6 mm).

In an example, the first portion 110 and second portion 114 can be directly adjacent to one another (i.e., distanced from each other by no more than a pitch distance of one of the two portions). Or, as shown in FIG. 1, the headless compression screw 100 can further include an third portion 118 that is positioned along the shaft 108 between the first portion 110 and second portion 114. As illustrated, in an example, the third portion 118 can include threads 120 that have an outer diameter $D_3$ that is less than the outer diameter $D_1$ of the threads 112 of first portion 110 and less than the outer diameter $D_2$ of the threads 116 of the second portion 114.

Headless compressions screws described herein can be manufactured using appropriate manufacturing techniques, such as machining. Specifically, the headless compression screws described herein can be manufactured using Swiss machining. The headless compression screws can generally comprise a high strength metal such as, for example and without limitation, titanium, titanium alloy, and the like.

Figure 4:
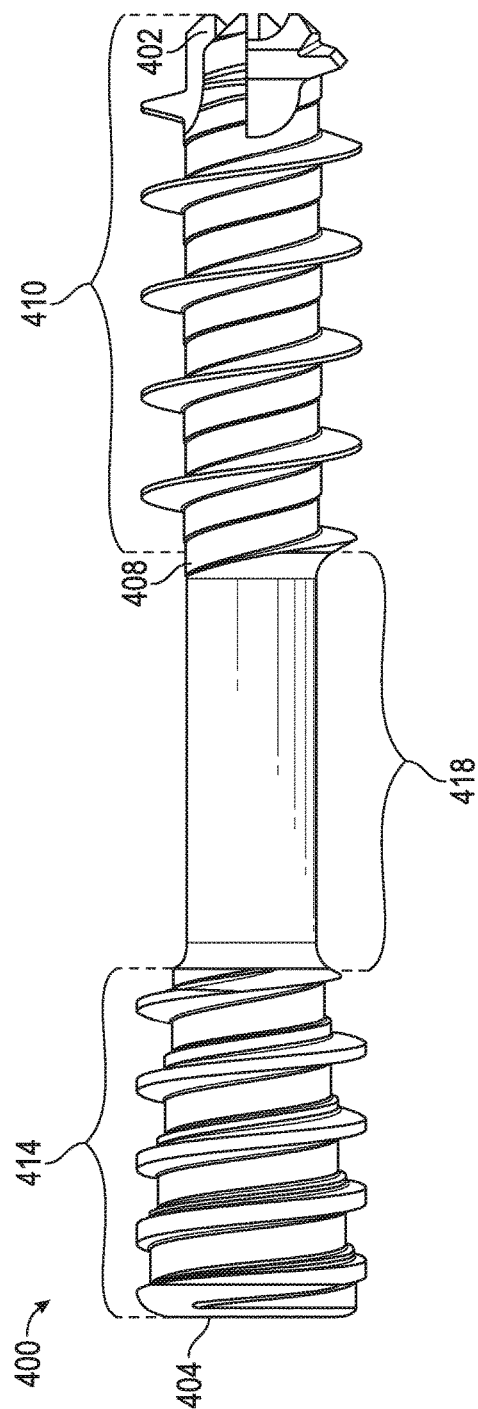
FIG. 4 is a side view of a compression screw according to an example of the present description.
Figure 5:
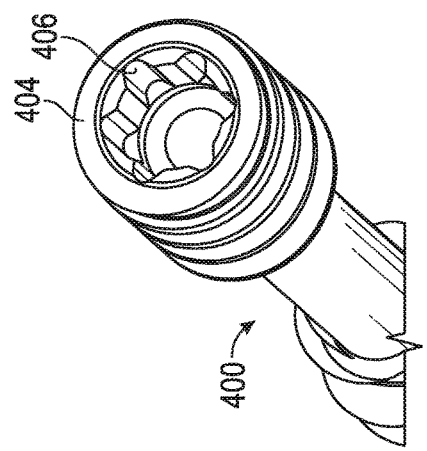
FIG. 5 is a perspective second end view of a compression screw according to an example of the present description.

In an embodiment, illustrated further below, the third portion can be unthreaded. Such an example is provided in FIG. 4. Here, headless compression screw 400 can include a shaft 408 extending from an insertion end 40 to an opposing driving end 404. The headless compression screw 400 can share many of the same features as compression screw 100, such as a first portion 410 and second portion 414 that can have like characteristics as first portion 110 and second portion 114 of FIG. 1. However, as illustrated, the third portion 418 of the present example is unthreaded. This construction can be beneficial in reducing the amount of bony growth around the third portion 418 of the screw 400 and can thus facilitate removal of the headless compression screw 400 after the fracture is healed. In an example, the headless nature of compression screws 100 and 400 can also ease removal and insertion of the screws. Headless compression screw 400 can, similar to the construction shown in FIG. 2, include a hex head for engaging with the driver. As shown in FIG. 5, the driving end 404 can include a driver engagement feature 406 that is a female six-point star feature, among other potential shapes.

As further illustrated in FIG. 1, the diameter of the second portion 114 of the shaft 108 can decrease from a first value to a second value as distance from the driving end 104 decreases. For instance, $DS_1 < DS_2 < DS_3$. The decrease can be such that the diameter of the shaft is tapered in the second portion by between 10° and 15° relative to the longitudinal axis 122 of the shaft. However, as further illustrated, the diameter $D_2$ of the outermost portion of the second threads 116 in the second portion 114 can remain constant as distance from the second end 104 increases. In an example, in the first portion 110, the diameter of the shaft $DS_4$ and the outermost portion of the first thread 114, $D_1$, remain constant throughout the first portion 110.

The headless compression screw 100 can have a length $L_1$ along the longitudinal axis 122 of the screw 100 and the first portion 110 can have a length $L_2$ along the longitudinal axis 122. The present inventors have discovered that an appropriate ratio of the length of the first portion 110 to the entire compression screw 100 can provide unique advantages. In an example, the first portion 110 has a length $L_2$ that is between about 30% and about 50% of the length $L_1$ of the headless compression screw 100. Further, the first portion 110 can have a length $L_2$ that is between about 35% and about 45% of the length $L_1$ of the headless compression screw 100, or a ratio of length $L_2$ that is between about 38% and about 42% of the length $L_1$. In an example, the ratio of $L_2$ to $L_1$ can be approximately 40%. The provided ratios can aid in providing a proportional torque to compression relationship, such as described further below.

Figure 6A:
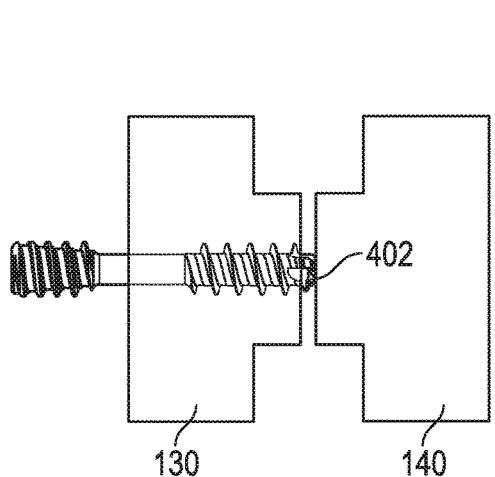
FIG. 6A-6D illustrates a side view of a compression screw reducing a fracture at various points in a procedure.
Figure 6B:
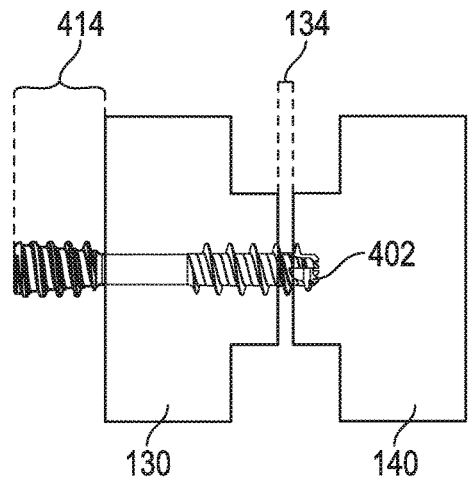
Figure 6C:
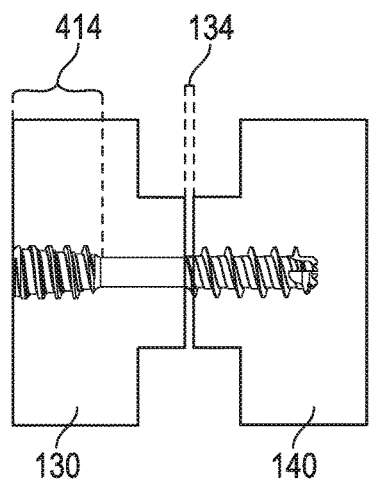
Figure 6D:
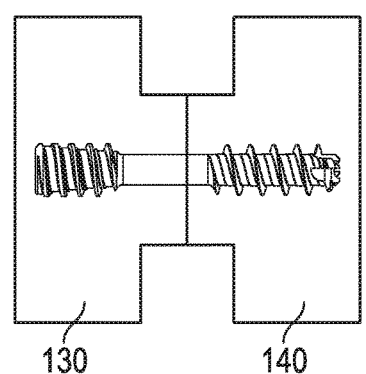

In an example, the headless compression screw 400 can be configured to reduce a fracture 134. An example of such a reduction (in various points in the procedure) illustrated in FIG. 6A-6D. The insertion end 402 of the headless compression screw is configured to enter and travel through a proximal bone fragment 130 and enter a distal bone fragment 140. As further illustrated in FIGS. 6C and 6D, driving the second portion 414 through the proximal bone fragment 130 compresses the proximal bone fragment 130 and distal bone fragment 140 towards one another, reducing the fracture 134 and urging the distal bone fragment and proximal bone fragment into contact. The headless compression screw 400 used in such a method can exhibit desirable tactile feedback qualities to the surgeon driving the screw. Specifically, the compression level between the proximal bone fragment 130 and distal bone fragment and the torque experienced by a driver that drives the compression screw 400 each proportionally increase from at or close to zero as the second portion drives through the proximal bone fragment.

Figure 7:
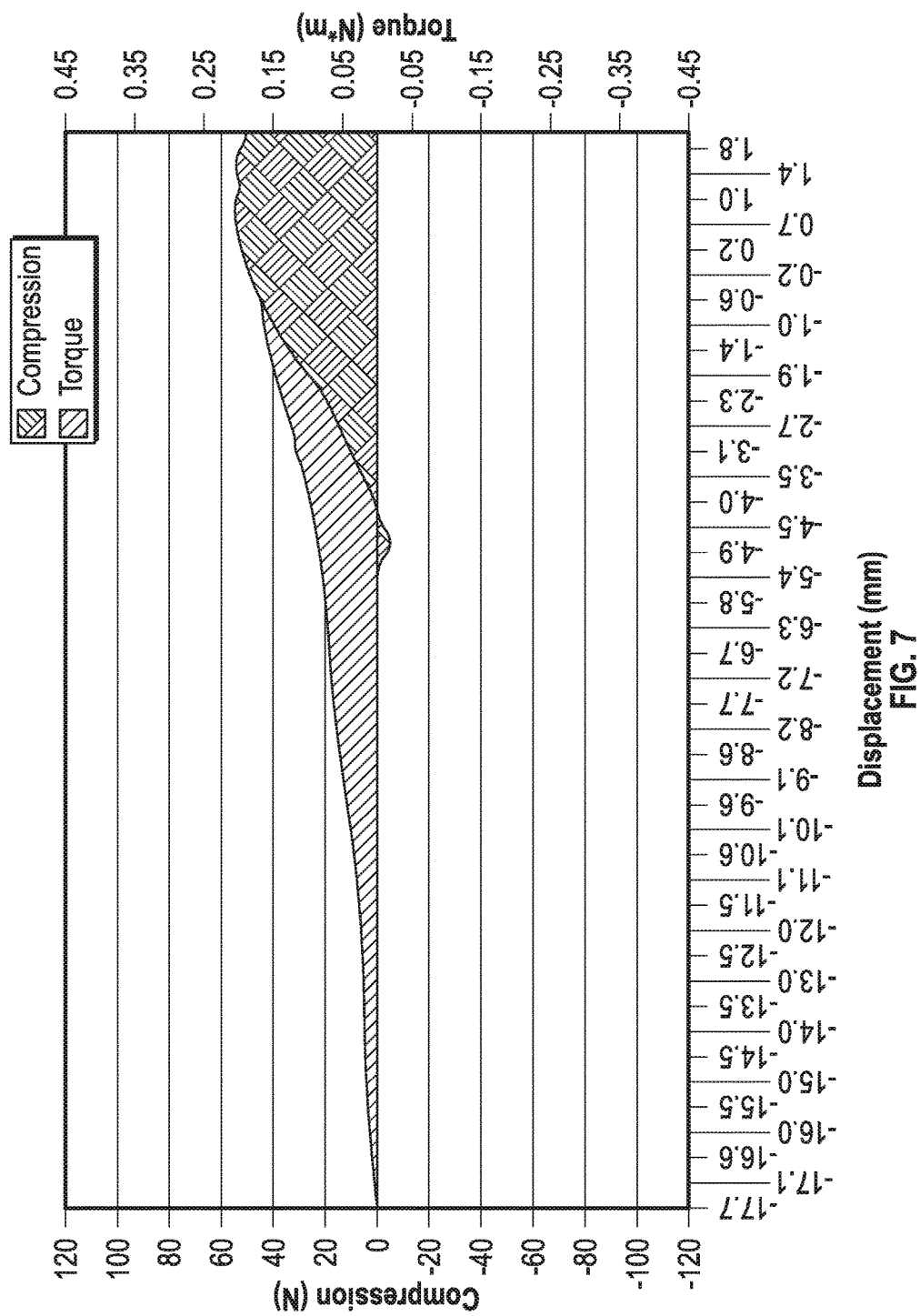
FIG. 7 is a graph of compression of fracture vs. torque experienced for a known compression screw.
Figure 8:
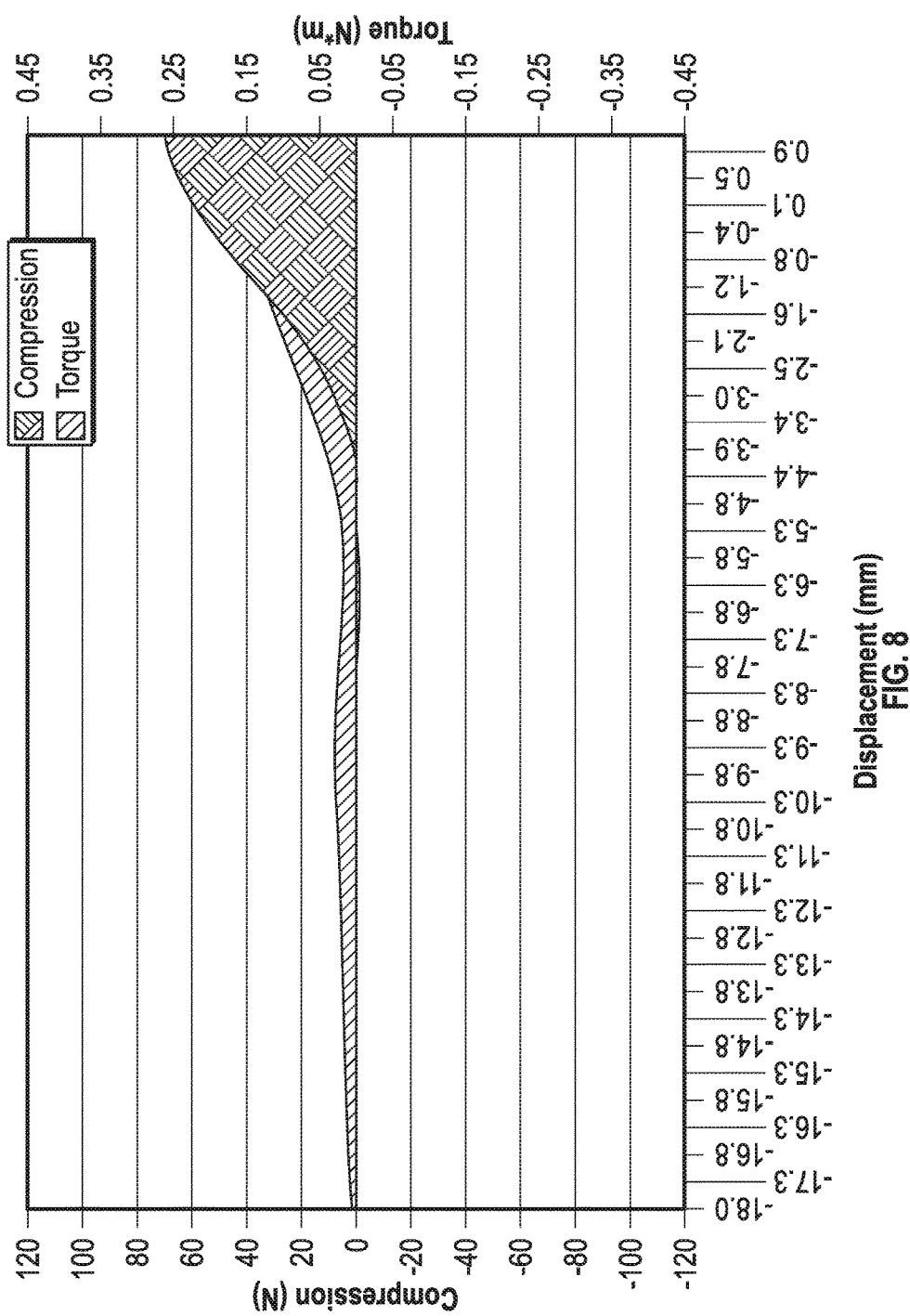
FIG. 8 is a graph of compression of fracture vs. torque experienced for a headless compression screw according to one example of the present description.

A graph illustrating the relationship of compression vs. torque force experienced by the driver of a conventional compression screw is illustrated in FIG. 7 and a graph of the compression vs. torque relationship of the presently described screw is presented in FIG. 8. As illustrated in FIG. 7, in the currently used compression screw the amount of torque experienced generally proportionally increases from the point where a insertion end of the compression screw is inserted into a proximal bone fragment (far left of graph) until the fracture has been fully reduced (i.e. it increases across the entirety of the insertion of the screw—far right of graph). As such, it is not clear to the surgeon driving the screw when compression of the fracture is occurring. In contrast, as shown in FIG. 8 the torque experienced by the presently described headless compression screw is minimal (near zero) and nearly constant from the point that the insertion end of the compression screw enters the proximal bone fragment (far left of graph), past the point that the insertion end enters the distal fragment, until the second portion (e.g. 114) of the compression screw enters the distal fragment. At that point the torque experienced by the driver begins to increase in a generally proportional manner, and the compression of the fracture also begins to occur in a proportional manner. Thus, the surgeon can better sense that compression has begun and that he or she needs to be sensitive to further advancement. At a given threshold of torque experienced, the surgeon will be aware that the fracture has been fully reduced and that he or she should stop driving the compression screw. As such the torque experienced vs. compression achieved are correlated.

Figure 9:
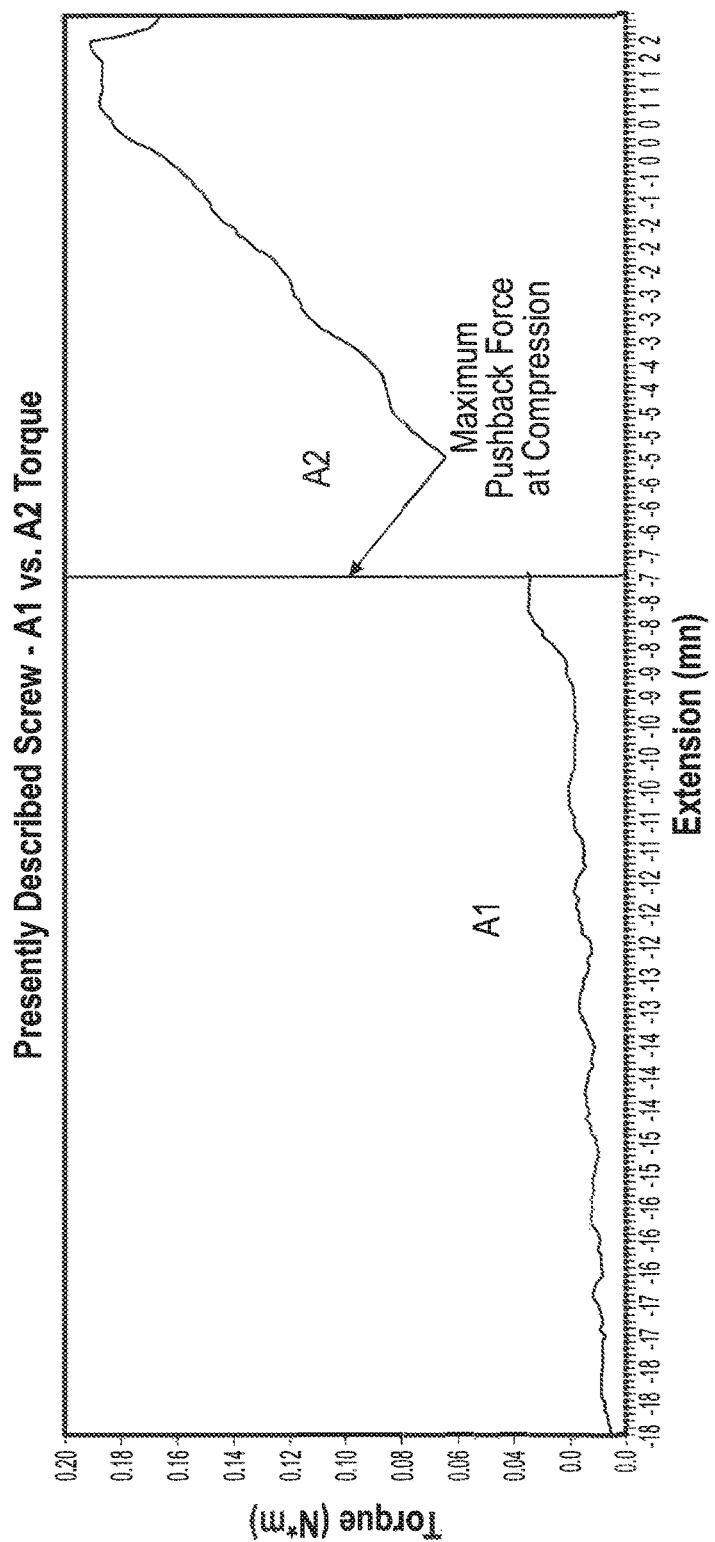
FIG. 9 is a graph of the work for a known compression screw during a first installation phase and a second installation phase.
Figure 10:
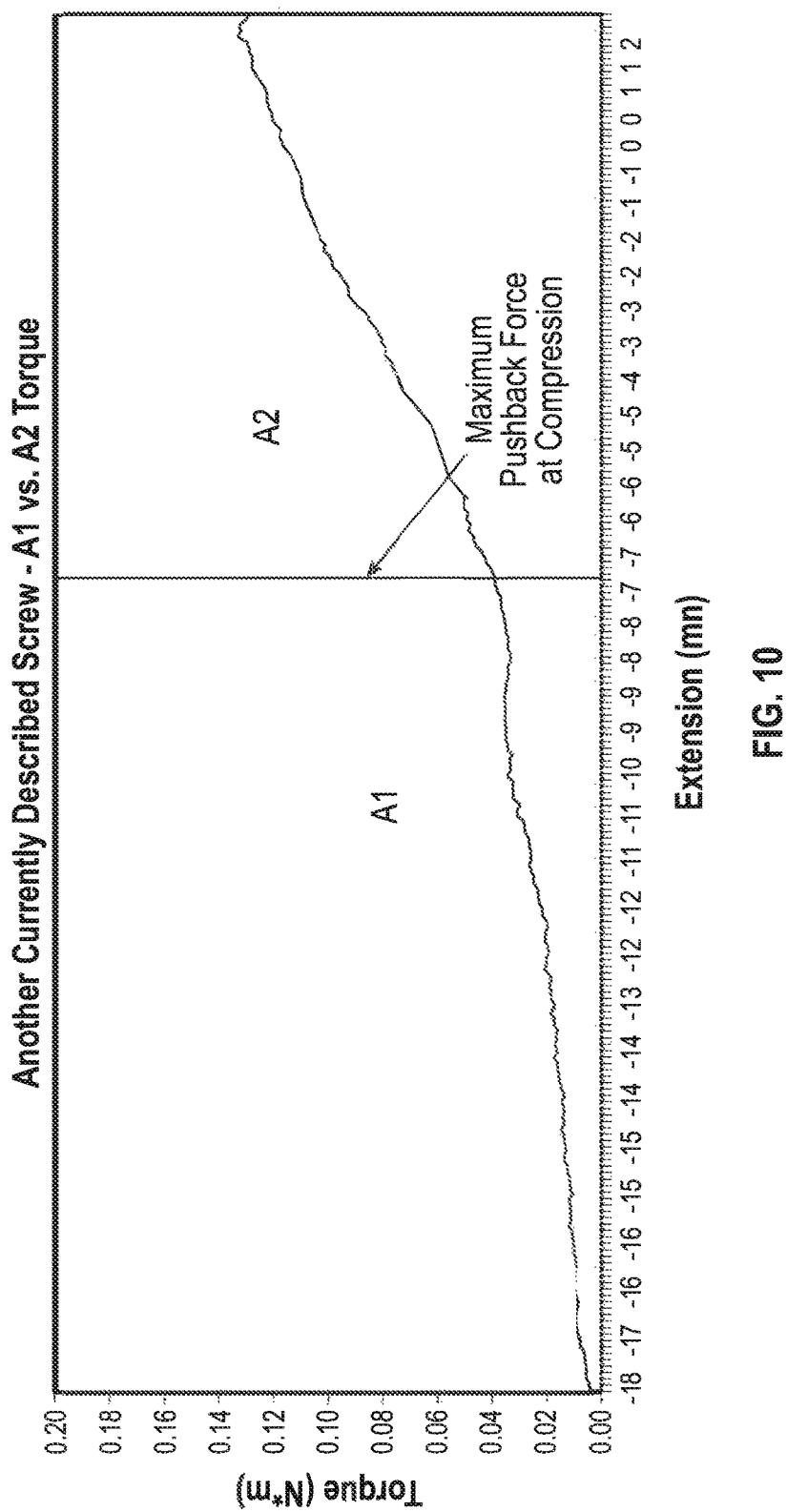
FIG. 10 is a graph of the work for a known compression screw during a first installation phase and a second installation phase.

In one example, the level of tactile feedback of the screw can be determined quantitatively and optimized by comparing the ratio of the slope of the best fit curve for the portion of the installation curve $S_1$ prior to the screw purchasing the distal bone fragment and the slope of the best fit curve for the portion of the installation curve $S_2$ subsequent to the screw purchasing the distal bone fragment. In an additional or alternative example illustrated in FIGS. 9 and 10, the level of tactile feedback of the screw can be determined quantitatively and optimized by comparing the ratio of the of the area under of the best fit curve for the portion of the installation curve $A_1$ prior to the screw purchasing the distal bone fragment and the area under the best fit curve for the portion of the installation curve $A_2$ subsequent to the screw purchasing the distal bone fragment, representing the work required to compress the distal and proximal bone fragments. The dividing point between the curves can be the point at which the highest negative force (or pushback) is recorded. Headless compression screws described herein exhibit higher $A_2$ values than $A_1$ values. In additional or alternative aspects, the ratios of $A_1:A_2$ values are greater than about 1:1.5, and, more particularly, greater than about 1:2. In additional or alternative aspects, the ratios of the ratios of $A_1:A_2$ values are from about 1:1.5 to about 1:10, more particularly, from about 1:1.8 to about 1:8, and, most particularly, from about 1:2 to about 1:6.

Figure 11:
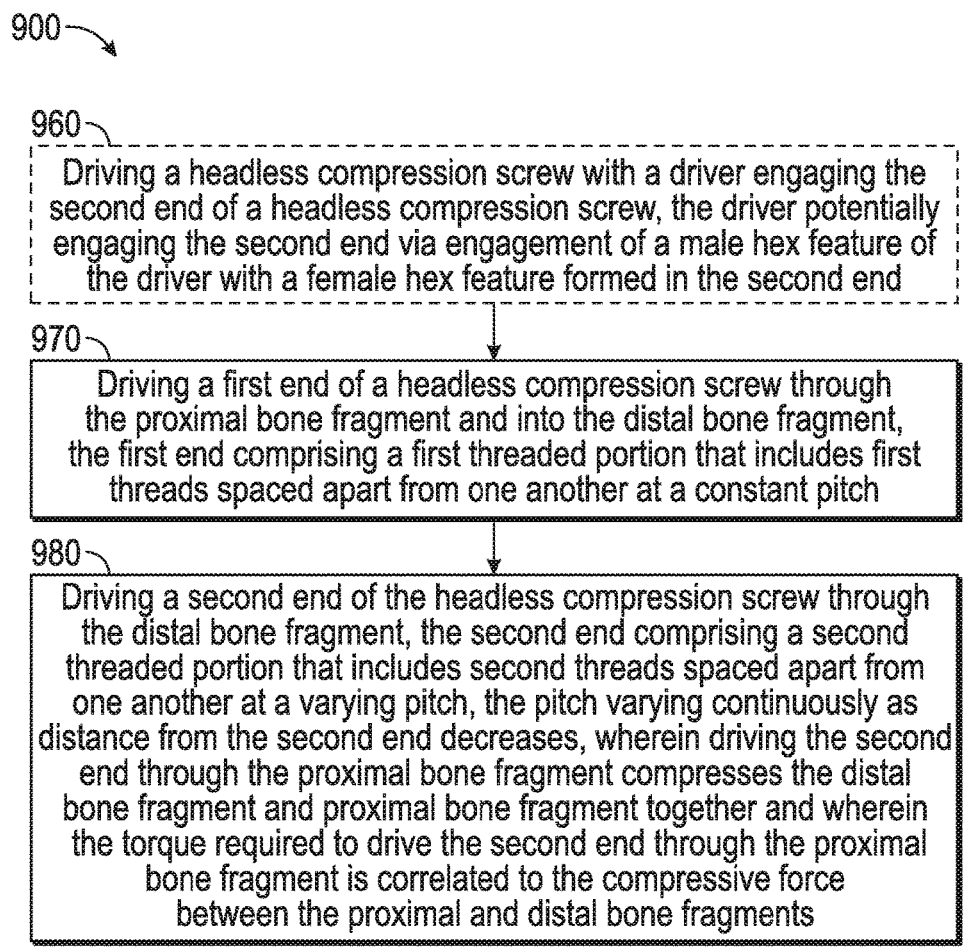
FIG. 11 is a block diagram of a method of reducing a fracture between a proximal and distal bone fragment according to one example of the present description.

FIG. 11 provides a block diagram of a potential method of inserting a headless compression screw such as described in the present description. As illustrated, the method can include driving an insertion end of a headless compression screw through the proximal bone fragment and into the distal bone fragment (process 970). The shaft can include a first portion that can include a first thread having a constant pitch. The method further can include driving a second end of the headless compression screw through the distal bone fragment (process 980). The second end can include a second portion that can include a second thread having a varying pitch. The pitch can vary continuously as distance from the second end decreases. Driving the second end through the proximal bone fragment can compress the distal bone fragment and proximal bone fragment together, and the torque required to drive the second end through the proximal bone fragment can be generally correlated to the compressive force between the proximal and distal bone fragments. As further illustrated in FIG. 11, optionally, the method can include driving the headless compression screw with a driver that engages with the second end of the headless compression screw (process 960). In one example, the driver engages the second end of the headless compression screw via engagement of a first male hex feature on the end of the driver with a female hex features formed into the second end. As noted above, other appropriate male and female features are contemplated for the second end of the headless compression screw (e.g. a cruciate shape, square shape, six-point star shape and the like).

VARIOUS NOTES & EXAMPLES

Example 1 is a headless compression screw, comprising: a shaft extending along a longitudinal axis from an insertion end to a driving end, the driving end comprising a driving engagement feature, the shaft comprising: a first portion extending from proximate the insertion end to a first intermediate point along the longitudinal axis, the first portion comprising a first thread extending across at least a portion thereof and having a constant pitch; a second portion extending from proximate the driving end to a second intermediate point that is proximal to the first intermediate point, the second portion comprising a second thread extending across at least a portion thereof and having a variable pitch that decreases from a first value proximate the second intermediate point to a second value proximate the driving end; wherein the work required to advance the shaft through a first bone tissue segment is less than the work required to advance the shaft through both the first bone tissue segment and a second bone tissue segment.

In Example 2, the subject matter of Example 1 optionally includes wherein, in use, the ratio of the work required to advance the first end of the shaft through the first bone tissue segment and the second bone tissue segment prior to engagement of the second portion and upon engagement of the second portion in the first bone tissue segment is at least about 1:1.5.

In Example 3, the subject matter of Example 2 optionally includes wherein, in use, the ratio of the work required to advance the first end of the shaft through the first bone tissue segment and the second bone tissue segment prior to engagement of the second portion and upon engagement of the second portion in the first bone tissue segment is at least about 1:2.

In Example 4, the subject matter of Example 3 optionally includes wherein, in use, the ratio of the work required to advance the first end of the shaft through the first bone tissue segment and the second bone tissue segment prior to engagement of the second portion and upon engagement of the second portion in the first bone tissue segment is from about 1:1.5 to about 1:10.

In Example 5, the subject matter of any one or more of Examples 1-4 optionally include wherein the first portion comprises a length that is between about 30% and about 50% of a length of the headless compression screw.

In Example 6, the subject matter of Example 5 optionally includes wherein the first portion comprises a length that is between about 35% and about 45% of a length of the shaft In Example 7, the subject matter of any one or more of Examples 1-6 optionally include wherein the first intermediate point and second intermediate point are directly adjacent to one another.

In Example 8, the subject matter of any one or more of Examples 1-7 optionally include a third portion positioned along the shaft between the first portion and second portion.

In Example 9, the subject matter of Example 8 optionally includes wherein the third portion is unthreaded.

In Example 10, the subject matter of any one or more of Examples 8-9 optionally include wherein the third portion comprises a third thread having an outer diameter less than an outer diameter of at least one of the first thread and the second thread.

In Example 11, the subject matter of any one or more of Examples 1-10 optionally include wherein a diameter of the second portion of shaft decreases from a first value to a second value as the distance from the driving end increases.

In Example 12, the subject matter of any one or more of Examples 1-11 optionally include wherein an outer diameter of the second thread and a diameter of the second portion are constant.

In Example 13, the subject matter of any one or more of Examples 1-12 optionally include wherein an outer diameter of the first thread and a diameter of the first portion are constant.

In Example 14, the subject matter of any one or more of Examples 1-13 optionally include wherein a largest pitch of the second portion is less than or equal to the constant pitch of the first portion.

In Example 15, the subject matter of any one or more of Examples 1-14 optionally include wherein the driver engagement feature comprises a female hex feature disposed in the driving end.

Example 16 is a system, comprising: a headless compression screw, comprising: a shaft extending along a longitudinal axis from an insertion end to a driving end, the driving end comprising a driving engagement feature, the shaft comprising: a first portion extending from proximate the insertion end to a first intermediate point along the longitudinal axis, the first portion comprising a first thread extending across at least a portion thereof and having a constant pitch; a second portion proximate extending from proximate the driving end to a second intermediate point that is proximate the first intermediate point, the second portion comprising a second thread extending across at least a portion thereof and having a variable pitch that decreases from a first value proximate the second intermediate point to a second value proximate the driving end; wherein the work required to advance the shaft through a first bone tissue segment is less than the work required to advance the shaft through both the first bone tissue segment and a second bone tissue segment and a driver for engaging the driver engagement feature.

In Example 17, the subject matter of Example 16 optionally includes wherein, in use, the ratio of the work required to advance the first end of the shaft through the first bone tissue segment and the second bone tissue segment prior to engagement of the second portion and upon engagement of the second portion in the first bone tissue segment is at least about 1:1.5.

In Example 18, the subject matter of Example 17 optionally includes wherein, in use, the ratio of the work required to advance the first end of the shaft through the first bone tissue segment and the second bone tissue segment prior to engagement of the second portion and upon engagement of the second portion in the first bone tissue segment is at least about 1:2.

In Example 19, the subject matter of Example 18 optionally includes wherein, in use, the ratio of the work required to advance the first end of the shaft through the first bone tissue segment and the second bone tissue segment prior to engagement of the second portion and upon engagement of the second portion in the first bone tissue segment is from about 1:1.5 to about 1:10.

In Example 20, the subject matter of any one or more of Examples 16-19 optionally include wherein the first portion comprises a length that is between about 30% and about 50% of a length of the headless compression screw.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A headless compression screw, comprising:
a shaft extending along a longitudinal axis from an insertion end to a driving end, the driving end comprising a driving engagement feature, the shaft comprising:
a first portion extending from proximate the insertion end to a first intermediate point along the longitudinal axis, the first portion comprising a first thread extending across at least a portion thereof at a constant pitch;
a second portion extending from proximate the driving end to a second intermediate point that is proximal to the first intermediate point, the second portion comprising a second thread that is separate from the first thread and extends across at least a portion of the second threaded portion at a variable pitch that decreases from a first value proximate the second intermediate point to a second value proximate the driving end, wherein a diameter of the shaft decreases and a height of the second thread increases to maintain a constant outer diameter of the second thread across a length of the shaft that corresponds to the second threaded portion as the distance from the second end increases, wherein the second threaded portion reduces and compresses a proximal and a distal bone fragment engaged by the headless compression screw, and wherein the second threaded portion is configured to provide tactile feedback to a user indicative of the compression applied to the proximal bone fragment and the distal bone fragment; and
an intermediate portion positioned along the shaft between the first threaded portion and the second threaded portion;
wherein a ratio of a first value of work required to advance the shaft through a first bone tissue segment and a second bone segment prior to engagement of the second portion to a second value of work required to advance the shaft through both the first bone tissue segment and a second bone tissue segment upon engagement of the second portion is at least 1:1.5.

2. The headless compression screw of claim 1, wherein the ratio of the first value of work to the second value of work is at least 1:2.

3. The headless compression screw of claim 1, wherein the ratio the first value of work to the second value of work is from 1:1.5 to about 1:10.

4. The headless compression screw of claim 1, wherein the first portion comprises a length that is between about 30% and about 50% of a length of the shaft.

5. The headless compression screw of claim 4, wherein the first portion comprises a length that is between about 35% and about 45% of the length of the shaft.

6. The headless compression screw of claim 1, wherein the third portion is unthreaded.

7. The headless compression screw of claim 1, wherein the third portion comprises a third thread having an outer diameter less than an outer diameter of at least one of the first thread and the second thread.

8. The headless compression screw of claim 1, wherein an outer diameter of the first thread and a diameter of the first portion are constant.

9. The headless compression screw of claim 1, wherein the driver engagement feature comprises a female hex feature disposed in the driving end.

10. A system, comprising:
a headless compression screw, comprising:
a shaft extending along a longitudinal axis from an insertion end to a driving end, the driving end comprising a driving engagement feature, the shaft comprising:
a first portion extending from proximate the insertion end to a first intermediate point along the longitudinal axis, the first portion comprising a first thread extending across at least a portion thereof at a constant pitch;
a second portion extending from proximate the driving end to a second intermediate point that is proximal to the first intermediate point, the second portion comprising a second thread that is separate from the first thread and extends across at least a portion of the second threaded portion at a variable pitch that decreases from a first value proximate the second intermediate point to a second value proximate the driving end, wherein a diameter of the shaft decreases and a height of the second thread increases to maintain a constant outer diameter of the second thread across a length of the shaft that corresponds to the second threaded portion as the distance from the second end increases, wherein the second threaded portion reduces and compresses a proximal and a distal bone fragment engaged by the headless compression screw, and wherein the second threaded portion is configured to provide tactile feedback to a user indicative of the compression applied to the proximal bone fragment and the distal bone fragment; and
an intermediate portion positioned along the shaft between the first threaded portion and the second threaded portion;
wherein a ratio of a first value of work required to advance the shaft through a first bone tissue segment and a second bone segment prior to engagement of the second portion to a second value of work required to advance the shaft through both the first bone tissue segment and a second bone tissue segment upon engagement of the second portion is at least 1:1.5; and
a driver for engaging the driver engagement feature.

11. The headless compression screw of claim 10, wherein the ratio of the first value of work to the second value of work is at least 1:2.

12. The headless compression screw of claim 10, wherein the ratio of the first value of work to the second value of work is from 1:1.5 to 1:10.

13. The headless compression screw of claim 10, wherein the first portion comprises a length that is between about 30% and about 50% of a length of the headless compression screw.

* * * * *